(12) United States Patent
He et al.

(10) Patent No.: US 11,663,894 B2
(45) Date of Patent: May 30, 2023

(54) METHOD FOR PROCESSING ALARMS OF MULTIPLE DEVICES AND CENTRAL DISPLAY DEVICE

(71) Applicant: SHENZHEN MINDRAY BIO-MEDICAL ELECTRONICS CO., LTD., Shenzhen (CN)

(72) Inventors: Xianliang He, Shenzhen (CN); Zehong Guan, Shenzhen (CN); Wenyu Ye, Shenzhen (CN); Zehui Sun, Shenzhen (CN); Chenming Ma, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 0 days.

(21) Appl. No.: 17/504,576

(22) Filed: Oct. 19, 2021

(65) Prior Publication Data
US 2022/0122439 A1  Apr. 21, 2022

(30) Foreign Application Priority Data
Oct. 20, 2020 (CN) .......................... 202011127970.X (51) Int. Cl.
*G08B 21/02* (2006.01)
*G08B 5/22* (2006.01)
(52) U.S. Cl.
CPC .............. *G08B 21/02* (2013.01); *G08B 5/22* (2013.01)

(58) Field of Classification Search
CPC .......... G08B 21/02; G08B 5/22; G16H 20/17; G16H 20/40; G16H 40/63; G16H 40/67; A61B 5/00; A61B 5/7445; A61B 5/746; A61M 1/1621; A61M 16/0051; A61M 2205/18; A61M 2230/205; A61M 2230/42; A61M 2230/005
See application file for complete search history.

(56) References Cited

U.S. PATENT DOCUMENTS

| 2016/0148496 A1* | 5/2016 | Meredith | G16H 40/67 340/286.07 |
| 2019/0130730 A1* | 5/2019 | Boyer | G16Z 99/00 |
| 2019/0259261 A1* | 8/2019 | Janssen | A61B 5/746 |

OTHER PUBLICATIONS

Extended European Search Report issued in related European Application No. 21203775.8, dated Feb. 18, 2022, 9 pages.

* cited by examiner

*Primary Examiner* — Brian Wilson
(74) *Attorney, Agent, or Firm* — Bayes PLLC (57) ABSTRACT

Disclosed are a method for processing alarms of multiple devices and a central display device. An association between the multiple devices in terms of alarm causes is determined; and when there is an association between at least two different devices in terms of alarm causes, alarms generated by the at least two different devices is optimized. By means of a root cause analysis on alarms generated by devices, levels of alarms are lowered, and medical care personnel can more easily view and target higher-level alarm that requires more attention, so that trouble of the medical care personnel is reduced.

20 Claims, 5 Drawing Sheets

METHOD FOR PROCESSING ALARMS OF MULTIPLE DEVICES AND CENTRAL DISPLAY DEVICE

CROSS-REFERENCE TO RELATED APPLICATION

The application claims the benefits of priority of Chinese Application No. 202011127970.X, filed Oct. 20, 2020, the content of which is incorporated by reference in its entirety.

TECHNICAL FIELD

The disclosure relates to a method for processing alarms of multiple devices and a central display device.

BACKGROUND

Physiological parameters of a person may reflect a physical condition of the person, and therefore, it is very important to monitor a patient. For example, patients should be monitored during intraoperative and postoperative conditions, trauma care, in a hyperbaric oxygen chamber and a delivery room, or in the case of coronary heart disease, a critically ill patient, a newborn, and a premature infant. In a monitoring process of some patients, devices such as monitors, ventilators, and infusion pumps are generally involved, and there may also be devices for treatment such as hemodialysis devices in an intensive care unit. In the monitoring process, when these devices detect a change in a physiological condition of a patient and determine that alarms need to be issued for such a change, these devices issue alarms to prompt medical care personnel to handle it in time. For example, when detecting that a heart rate of the patient is excessively high or excessively low, or that a blood oxygen parameter of the patient is excessively low, or that a pulse of the patient is not found, or that a respiratory rate of the patient is excessively high or excessively low, the devices may issue alarms. Alarms may be issued due to a change in the patient's own physiological condition, or due to technical causes of the devices, for example, lead-off caused by replacement of an electrocardiogram electrode pad, and pulse searching or pulselessness caused by a poor contact of a blood oxygen probe. These alarms, that is, physiological alarms and technical alarms, are issued in the order of occurrence. If a large number of alarms are issued in a short period of time, it may bring some trouble to the medical care personnel, and the medical care personnel cannot quickly identify, in real time, alarms indicating that the patient's life is in danger. For example, the patient's physiological condition changes over a period of time and causes a heart rate and respiratory rate to fluctuate around a heart rate alarm threshold and a respiratory rate alarm threshold, during which many devices are operated, leading to a large number of limit-exceeding alarms of the heart rate and the respiratory rate as well as a large number of device technical alarms generated during this period of time.

SUMMARY

Considering that multiple alarms generated within a period of time cause trouble and inconvenience to medical care personnel, the disclosure provides a method for processing alarms of multiple devices and a central display device, which are specifically described as follows.

According to a first aspect, an embodiment provides a method for processing alarms of multiple devices, which is used for processing multiple alarms generated by multiple devices configured to monitor and/or treat a patient. The method for processing alarms of multiple devices includes:

obtaining, in real time, the multiple alarms generated by the multiple devices, or obtaining the multiple alarms generated by the multiple devices within a preset period;

determining an association between the multiple devices in terms of alarm causes;

and when at least two different devices of the multiple devices have the association in terms of alarm causes, optimizing alarm(s) generated by the at least two different devices.

In an embodiment, optimizing alarm(s) generated by the at least two different devices comprises:

determining, between the at least two devices having the association in terms of alarm causes, a rear-end device at a rear end of an alarm transfer chain corresponding to the alarms generated by the at least two devices; and lowering an initial level of an alarm generated by the rear-end device.

In an embodiment, an initial level of each of the multiple alarms is related to an alarm level of a parameter, and the alarm level of the parameter is determined by a value of the parameter.

In an embodiment, the method for processing alarms of multiple devices further includes displaying the optimized alarm(s).

In an embodiment, the method for processing alarms of multiple devices further includes sorting the multiple alarms according to levels of the multiple alarms, and then displaying the sorted alarms.

In a second aspect, an embodiment provides a method for processing alarms of multiple devices, which is used for processing multiple alarms generated by multiple devices configured to monitor and/or treat a patient. The method for processing alarms of multiple devices includes:

obtaining, in real time, the multiple alarms generated by the multiple devices, or obtaining the multiple alarms generated by the multiple devices within a preset period;

for alarm(s) generated by a first device of the multiple devices, determining whether a first alarm generated by the first device is caused by a change in a setting parameter of a second device of the multiple devices; and if the first alarm generated by the first device is caused by the change in the setting parameter of the second device, lowering an initial level of the first alarm generated by the first device.

In an embodiment, determining whether a first alarm generated by the first device is caused by a change in a setting parameter of a second device of the multiple devices comprises:

determining whether there is an alarm transfer chain corresponding to the first alarm generated by the first device;

if there is an alarm transfer chain corresponding to the first alarm generated by the first device, determining whether the first device is at a rear end of the alarm transfer chain;

if the first device is at the rear end of the alarm transfer chain, determining whether the setting parameter of the second device is changed, the second device being a front-end device on the alarm transfer chain corresponding to the first alarm; and if the setting parameter is changed, determining that the first alarm generated by the first device is caused by the change in the setting parameter of the second device.

In an embodiment, an initial level of each of the multiple alarms is related to an alarm level of a parameter, and the alarm level of the parameter is determined by a value of the parameter.

In an embodiment, the method for processing alarms of multiple devices further includes displaying the first alarm, the initial level of the first alarm being lowered.

In an embodiment, the method for processing alarms of multiple devices further includes sorting the multiple alarms according to levels of the multiple alarms, and displaying the sorted alarms.

In a third aspect, an embodiment provides a central display device, the central display device establishing a connection to multiple devices configured to monitor and/or treat a patient, and configured to generate multiple alarms and transfer the multiple alarms to the central display device. The central display device includes a display, a processor, a memory, and multiple program instructions stored in the memory, and the processor invokes the multiple program instructions to perform the following steps:

obtaining, in real time, the multiple alarms generated by the multiple devices, or obtaining the multiple alarms generated by the multiple devices within a preset period;

determining an association between the multiple devices in terms of alarm causes;

and when at least two different devices of the multiple devices have the association in terms of alarm causes, optimizing alarm(s) generated by the at least two different devices.

In an embodiment, optimizing alarm(s) generated by the at least two different devices comprises:

determining, between the at least two devices having the association in terms of alarm causes, a rear-end device at a rear end of an alarm transfer chain corresponding to the alarms generated by the at least two devices; and lowering an initial level of an alarm generated by the rear-end device.

In an embodiment, an initial level of each of the multiple alarms is related to an alarm level of a parameter, and the alarm level of the parameter is determined by a value of the parameter.

In an embodiment, the display is configured to display the optimized alarm(s).

In an embodiment, the processor invokes the multiple program instructions to further sort the multiple alarms according to levels of the multiple alarms; and the display is configured to display the sorted alarms.

In a fourth aspect, an embodiment provides a central display device, the central display device establishing a connection to multiple devices configured to monitor and/or treat a patient, and configured to generate multiple alarms and transfer the multiple alarms to the central display device. The central display device includes a display, a processor, a memory, and multiple program instructions stored in the memory, and the processor invokes the multiple program instructions to perform the following steps:

obtaining, in real time, the multiple alarms generated by the multiple devices, or obtaining the multiple alarms generated by the multiple devices within a preset period;

for alarm(s) generated by a first device of the multiple devices, determining whether a first alarm generated by the first device is caused by a change in a setting parameter of a second device of the multiple devices; and if the first alarm generated by the first device is caused by the change in the setting parameter of the second device, lowering an initial level of the first alarm generated by the first device.

In an embodiment, determining whether a first alarm generated by the first device is caused by a change in a setting parameter of a second device of the multiple devices comprises:

determining whether there is an alarm transfer chain corresponding to the first alarm generated by the first device;

if there is an alarm transfer chain corresponding to the first alarm generated by the first device, determining whether the first device is at a rear end of the alarm transfer chain;

if the first device is at the rear end of the alarm transfer chain, determining whether the setting parameter of the second device is changed, wherein the second device is a front-end device on the alarm transfer chain corresponding to the first alarm; and if the setting parameter is changed, determining that the first alarm generated by the first device is caused by the change in the setting parameter of the second device.

In an embodiment, an initial level of each of the multiple alarms is related to an alarm level of a parameter, and the alarm level of the parameter is determined by a value of the parameter.

In an embodiment, the display is configured to display the optimized alarm(s).

In an embodiment, the processor invokes the multiple program instructions to further sort the multiple alarms according to levels of the multiple alarms; and the display is configured to display the sorted alarms.

According to a fifth aspect, an embodiment provides a computer-readable storage medium, including a program, which is executable by a processor to implement the method described in any one of the embodiments herein.

According to the method for processing alarms of multiple devices, the central display device, and the computer-readable storage medium in the foregoing embodiments, by means of a root cause analysis on alarm information generated by devices, levels of alarms are lowered, and medical care personnel can more easily view and locate higher-level alarm that requires more attention, so that trouble of the medical care personnel is reduced.

DETAILED DESCRIPTIONS

The disclosure will be further described in detail below through specific implementations in conjunction with the accompanying drawings. Associated similar element reference numerals are used for similar elements in different implementations. In the following embodiments, many details are described such that the disclosure may be better understood. However, it may be effortlessly appreciated by a person skilled in the art that some of the features may be omitted, or may be substituted by other elements, materials, and methods in different cases. In certain cases, some operations involved in the disclosure are not displayed or described in the specification, which is to prevent a core part of the disclosure from being obscured by too much description. Moreover, for a person skilled in the art, the detailed description of the involved operations is not necessary, and the involved operations can be thoroughly understood according to the description in the specification and general technical knowledge in the art.

In addition, the characteristics, operations, or features described in the specification may be combined in any appropriate manner to form various implementations. Meanwhile, the steps or actions in the method description may also be exchanged or adjusted in order in a way that is obvious to a person skilled in the art. Therefore, the various orders in the specification and the accompanying drawings are merely for the purpose of clear description of a certain embodiment and are not meant to be a necessary order unless it is otherwise stated that a certain order must be followed.

The serial numbers themselves for the components herein, for example, "first" and "second", are merely used to distinguish described objects, and do not have any sequential or technical meaning. Moreover, as used in the disclosure, "connection" or "coupling", unless otherwise stated, includes both direct and indirect connections (couplings).

A device, mentioned in the disclosure, for monitoring and/or treating a patient is typically a device that can at least measure a physiological parameter of the patient. The device usually can issue an alarm according to an obtained physiological parameter of the patient. For example, the device compares the obtained physiological parameter of the patient with a known set range or value, and issues an alarm if the physiological parameter is not within a normal range. The device may be, for example, a monitor, a ventilator, an anesthesia machine, an infusion pump, a syringe pump, a hemodialysis device, etc.

Figure 1:
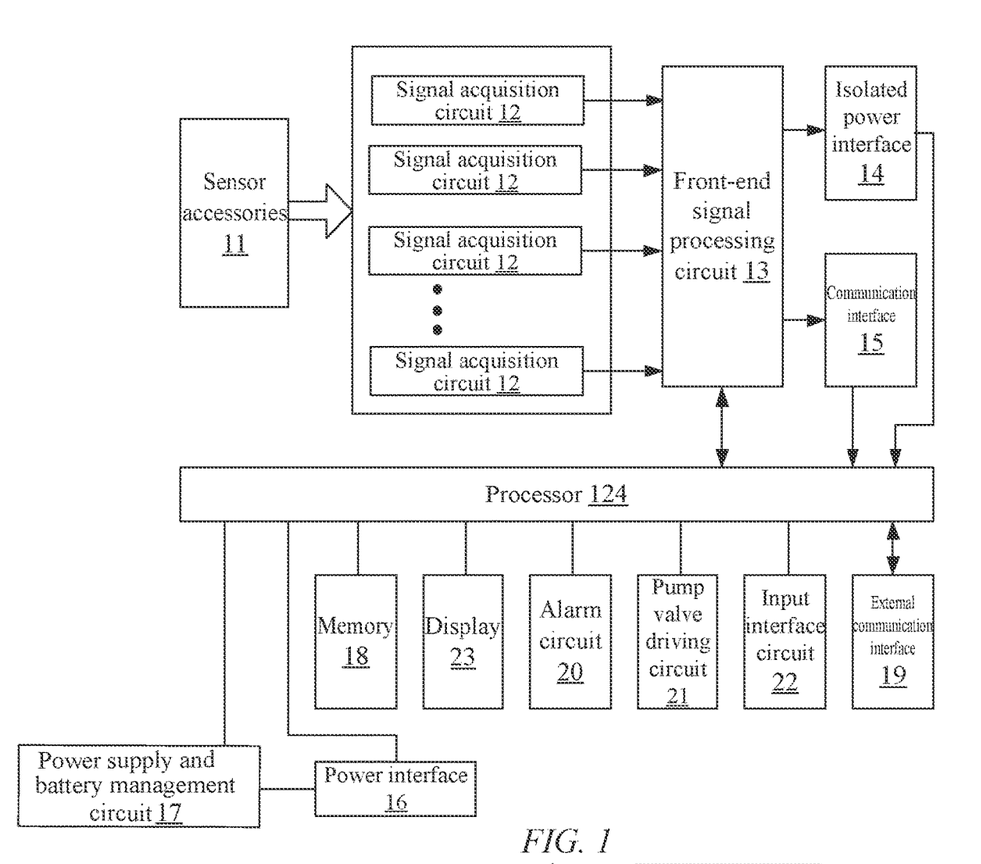
FIG. 1 is a schematic structural diagram of a monitor according to an embodiment.

FIG. 1 shows an example of a monitor. In some embodiments, the monitor may have an independent housing. A housing panel may have a sensor interface area where multiple sensor interfaces may be integrated and configured to be connected to various external physiological parameter sensor accessories 11. The housing panel may further include one or more of a small IXD display region, a display 23, an input interface circuit 22, an alarm circuit 20 (such as an LED alarm area), and the like. In some embodiments, the monitor further has an external communication interface 19 and a power interface 16 for communicating with a main unit and drawing power from the main unit. In some embodiments, the monitor may also support a built-out parameter module. The parameter module may be plugged in to form a plug-in monitor, and is used as a part of the monitor. Alternatively, the parameter module may be connected to the main unit by means of a cable, and the built-out parameter module is used as an external accessory of the monitor. Circuits of the monitor may be placed in the housing, and may include signal acquisition circuits 12 corresponding to one or more physiological parameters and a front-end signal processing circuit 13. The signal acquisition circuit 12 may be selected from an electrocardiogram circuit, a respiration circuit, a body temperature circuit, a blood oxygen circuit, a non-invasive blood pressure circuit, an invasive blood pressure circuit, and the like. These signal acquisition circuits 12 are electrically connected to respective sensor interfaces, so as to be electrically connected to sensor accessories 11 corresponding to different physiological parameters. Output ends of the signal acquisition circuits 12 are coupled to the front-end signal processing circuit 13, a communication interface of the front-end signal processing circuit 13 is coupled to a processor 124, and the processor 124 is electrically connected to the external communication interface 19 and the power interface 16. The sensor accessories 11 and the signal acquisition circuits 12 corresponding to various physiological parameters may be general-purpose circuits in the prior art. The front-end signal processing circuit 13 completes sampling and analog-to-digital conversion of output signals of the signal acquisition circuits 12, and outputs a control signal to control a measurement process of a physiological signal. These parameters include but are not limited to: electrocardiogram, respiration, body temperature, blood oxygen, non-invasive blood pressure, and invasive blood pressure. The front-end signal processing circuit 13 may be implemented by using a single-chip microcomputer or other semiconductor devices, for example, a mixed-signal single-chip microcomputer such as LPC2136 of PHILIPS or ADuC7021 by ADI, or may be implemented by using an ASIC or an FPGA. The front-end signal processing circuit 13 may be powered by an isolated power supply, and data sampled is sent to the processor 124 by means of an isolated communication interface after simple processing and packetization. For example, the front-end signal processing circuit 13 may be coupled to the processor 124 by means of an isolated power interface 14 and a communication interface 15. A reason for which the front-end signal processing circuit 13 is powered by an isolated power supply is that a DC/DC power supply isolated by a transformer has a function of isolating a patient from a power supply device, the main purposes including: (1) isolating the patient, and enabling an application part to be floating by isolating the transformer, so that a leakage current of the patient is small enough; and (2) preventing a voltage or energy during defibrillation or electrotome application from affecting a board and a device of an intermediate circuit such as a main control board (guaranteed by a creepage distance and an electrical clearance). Certainly, the front-end signal processing circuit 13 may alternatively be connected to the processor 124 by means of a cable. The processor 124 completes calculation of the physiological parameter, and sends a calculation result and waveform of the parameter to the main unit (such as a main unit with a display, a PC, and a central display device) through the external communication interface 19. The processor 124 may be directly connected to the external communication interface 19 by means of a cable to perform communication and may be directly connected to the power interface 16 by means of a cable to draw power. The monitor may further include a power supply and battery management circuit 17.

The power supply and battery management circuit 17 draws power from the main unit through the power interface 16, and supplies power to the processor 124 after processing such as rectification and filtering. The power supply and battery management circuit 17 may further monitor, manage, and protect the power drawn from the main unit through the power interface 16. The external communication interface 19 may be one of or a combination of the Ethernet, a token ring, a token bus, and a local area network interface composed of a fiber distributed data interface (FDDI) for a backbone network of these three networks, or may be one of or a combination of wireless interfaces such as an infrared interface, Bluetooth, Wi-Fi, and WMTS communication interfaces, or may be one of or a combination of wired data connection interfaces such as RS232 and USB interfaces. The external communication interface 19 may alternatively be one of a wireless data transmission interface and a wired data transmission interface or a combination thereof. The main unit may be any computer device such as a main unit of the monitor, a computer, etc., and can form a monitoring system once installed with a corresponding software. The main unit may alternatively be a communication device such as a mobile phone, and the monitor sends data to a Bluetooth-enabled mobile phone by using a Bluetooth interface, so as to implement remote transmission of data. After completing calculation of the physiological parameter, the processor 124 may further determine whether the physiological parameter is anomalous, and if the physiological parameter is anomalous, it may issue an alarm by means of the alarm circuit 20. A memory 18 may store intermediate and final data of the monitor, and store program instructions or code executed by the processor 124 and the like. If the monitor is available for blood pressure measurement, the monitor may further include a pump valve driving circuit 21. The pump valve driving circuit 21 is configured to perform inflation or deflation operations under the control of the processor 124.

The monitor can monitor the physiological parameter of the patient, and provides an effective means for medical care personnel to comprehensively and intuitively know the patient's conditions in time. The monitor is generally divided into two types: a bedside monitor and a transfer monitor. The bedside monitor is a machine disposed beside a hospital bed and connected to a patient, which can continuously monitor various physiological parameters or statuses of the patient to display alarms or records. In practical cases, during a hospitalization period, as a condition of the patient changes, the patient may be transferred between different beds in the same department, or may need to go out for examination, or may be transferred to a different department. When being transferred from one location to another, the monitor of the patient is switched from the bedside monitor to the transfer monitor.

Figure 2:
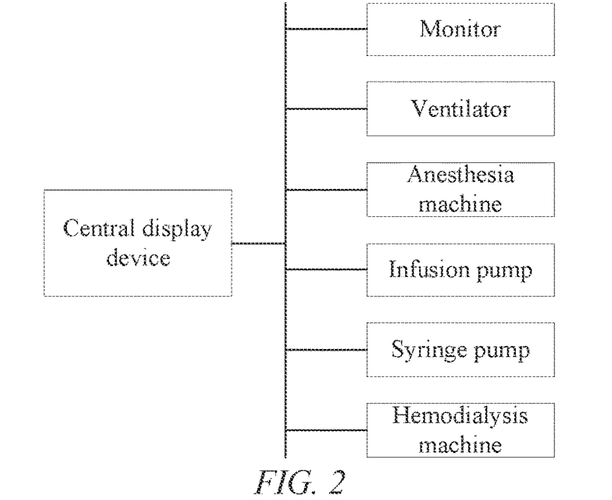
FIG. 2 is a schematic diagram in which a central display device is communicatively connected to a monitor, a ventilator, an anesthesia machine, an infusion pump, a syringe pump, and a hemodialysis device according to an embodiment.

Referring to FIG. 2, to facilitate medical care personnel in remotely learning a physiological condition of a patient, a central display device may be introduced. In some embodiment, the central display device can store data of the monitor and other devices, mentioned in the disclosure, for monitoring and/or treating a patient, such as a ventilator, an anesthesia machine, an infusion pump, a syringe pump, and a hemodialysis device, and can manage patient information and nursing information centrally, which facilitates storage of historical data and management of alarm information. Specifically, the central display device may establish a connection to one or more devices, mentioned in the disclosure, for monitoring and/or treating a patient, each of the devices that monitor and/or treat the patient can generate alarm information and transfer the alarm information to the central display device. The central display device may be connected to these devices in a wired manner or in a wireless manner.

Figure 3:
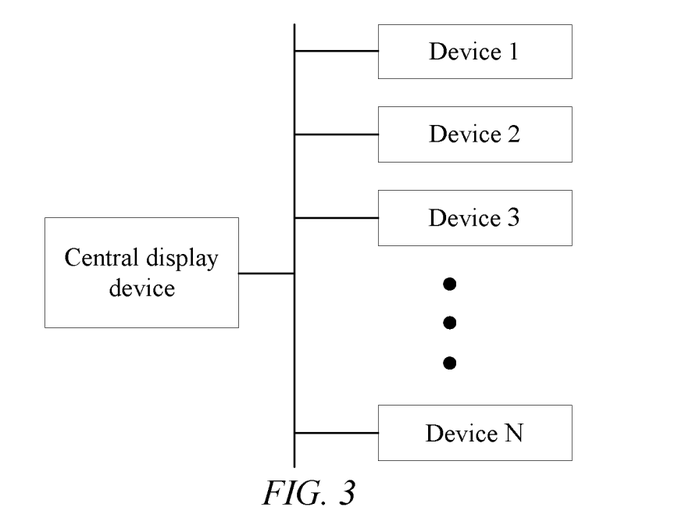
FIG. 3 is a schematic diagram in which a central display device is communicatively connected to multiple devices that monitor and/or treat a patient according to an embodiment.
Figure 4:
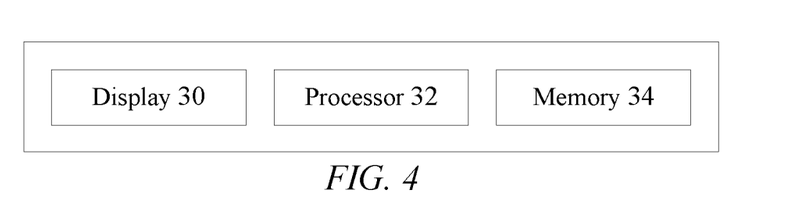
FIG. 4 is a schematic structural diagram of a central display device according to an embodiment.

Referring to FIG. 3, a central display device in the disclosure can process alarm information generated by devices for monitoring and/or treating a patient referring to as device 1, device 2, device 3, . . . , and device N in the figure, and optimize the alarm information, so that even when a large amount of alarm information appears over a period of time, especially over a short period of time, medical care personnel can quickly target the alarm information that requires attention. Certainly, it can be understood that the device 1, the device 2, the device 3, . . . , and the device N in FIG. 3 are all used for monitoring and/or treating a same patient, that is, alarm information generated by the device 1, the device 2, the device 3, . . . , and the device N in FIG. 3 are for a same object, namely, a same patient. Referring to FIG. 4, a central display device in some embodiments includes a display 30, a processor 32, and a memory 34. The memory 34 stores a number of program instructions 36. In other words, the central display device further includes a number of program instructions 36 stored in the memory 34. The program instructions 36 can be invoked by the processor 32 to perform corresponding steps, and implement corresponding functions, which are specifically described as follows.

Figure 5:
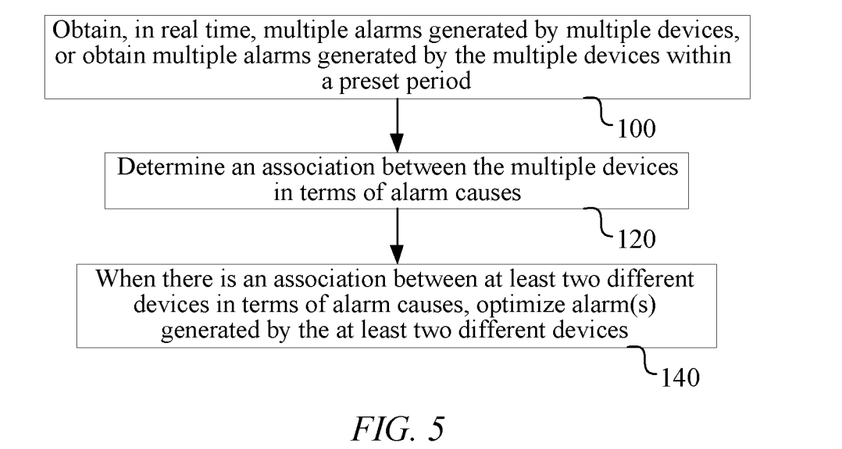
FIG. 5 is a flowchart of a method for processing alarms of multiple devices according to an embodiment.
Figure 6:
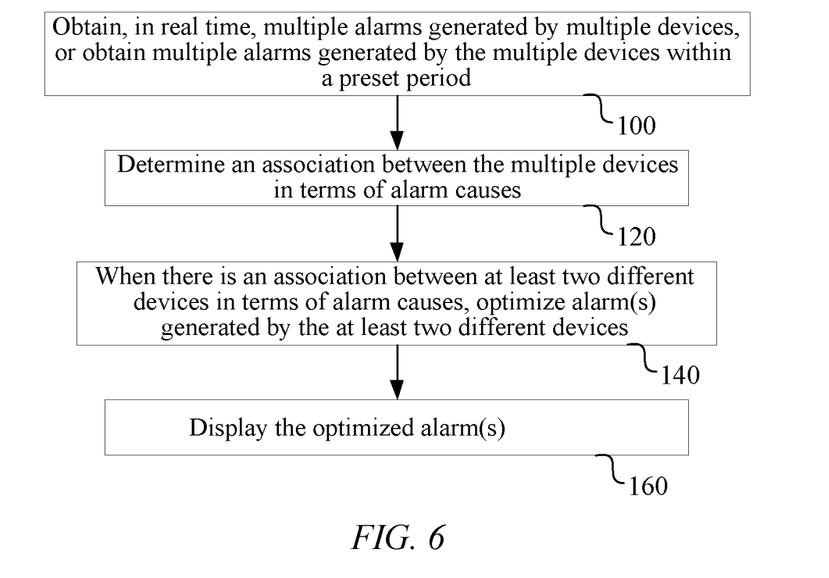
FIG. 6 is a flowchart of a method for processing alarms of multiple devices according to another embodiment.
Figure 7:
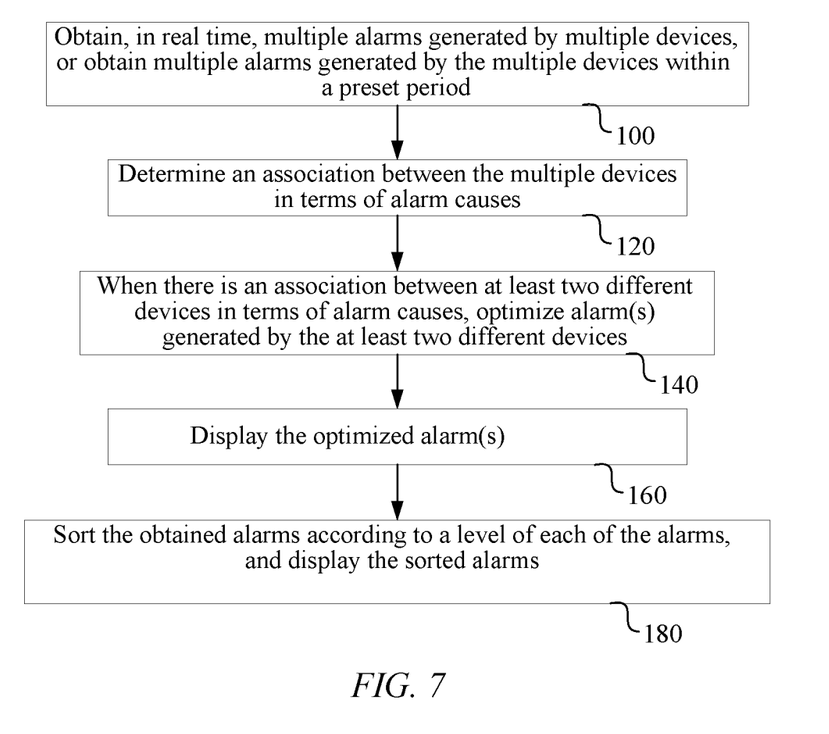
FIG. 7 is a flowchart of a method for processing alarms of multiple devices according to still another embodiment.

Referring to FIGS. 5, 6, and 7, in some embodiments, the processor 32 can invoke the number of program instructions 36 described above to further perform the following steps.

In step 100, multiple pieces of alarm information generated by multiple devices are obtained in real time, or multiple pieces of alarm information generated by the multiple devices within a preset time period are obtained.

It can be understood that the multiple devices herein are devices that establish a connection to a central display device and can generate alarm information and transfer the alarm information to the central display device. These devices monitor and/or treat a same patient.

In step 120, an association between the multiple devices in terms of alarm causes is determined. That is, when the central display obtains the alarm information sent by the multiple devices, the association between the multiple devices in terms of alarm causes is determined, so as to perform subsequent optimization.

The association between any two devices in terms of alarm causes means that alarm information generated by one of the devices is caused by the other device. For example, alarm information generated by one of the devices is caused by a change in a setting parameter of the other device. Such a change of the setting parameter may be a change caused by self-adaptive adjustment of the device itself, or a change caused by a user operating the device. It can be seen that such an association reflects a causal relationship in alarm information.

For example, reset of a respiratory rate for a ventilator may result in a respiratory alarm of a monitor. Certainly, the ventilator itself may also issue a respiratory alarm. In this case, it is considered in the disclosure that there is an association between the reset of the respiratory rate for the ventilator and the respiratory alarm of the monitor in terms of alarm causes, and the respiratory alarm generated by the monitor is caused by the change in the setting parameter, namely, the respiratory rate, of the ventilator.

For another example, a low respiratory rate set for a ventilator may result in an alarm of the monitor that a blood oxygen value is excessively low. Certainly, the ventilator itself may also issue an alarm that a blood oxygen value is excessively low. Therefore, it is considered in the disclosure that there is an association between the excessively low respiratory rate set for the ventilator and the alarm of the monitor that the blood oxygen value is excessively low in terms of alarm causes, and the alarm generated by the monitor that the blood oxygen value is excessively low is caused by the change in the setting parameter, namely, the respiratory rate, of the ventilator.

For still another example, changes in setting parameters such as a hemodialysis dose of a hemodialysis device leads to infusion of a patient with a large amount of liquid, which may result in alarms of the monitor related to body temperature and excessively low blood oxygen value. Certainly, the hemodialysis device itself may also issue alarms related to body temperature and excessively low blood oxygen value. Then, it is considered that there is an association between the increased hemodialysis dose of the hemodialysis device and alarms related to body temperature and excessively low blood oxygen value in terms of alarm causes, and the alarms related to body temperature and excessively low blood oxygen value are caused by the increased setting parameter, that is, the increased hemodialysis dose of the hemodialysis device.

Whether there is an association between two devices in terms of alarm causes may be determined by the processor 32 through real-time logic, or may be determined by the processor 32 querying a predefined association. For example, a number of associations are predefined, such as association 1: association between the respiratory rate for the ventilator and the respiratory alarm of the monitor in terms of alarm causes; association 2: association between the excessively low respiratory rate for the ventilator and the alarm of the monitor that the blood oxygen value is excessively low in terms of alarm causes; association 3: association between the increased hemodialysis dose of the hemodialysis device and the alarm related to body temperature of the monitor in terms of alarm causes; and association 4: association between the increased hemodialysis dose of the hemodialysis device and the alarm of the monitor that the blood oxygen value is excessively low in terms of alarm causes; etc.

In step 140, when there is an association between at least two different devices in terms of alarm causes, alarm information generated by the at least two different devices is optimized. In some specific embodiments, in step 140, a rear-end device at a rear end of an alarm transfer chain corresponding to the generated alarm information is determined in the at least two different devices that have an association in terms of alarm causes; and then an initial alarm level of alarm information generated by the rear-end device is lowered.

For example, reset of a respiratory rate for a ventilator may result in a respiratory alarm of a monitor. Certainly, the ventilator itself may also issue a respiratory alarm. In this case, it is considered in the disclosure that there is an association between the reset of the respiratory rate for the ventilator and the respiratory alarm of the monitor in terms of alarm causes, and the respiratory alarm generated by the monitor is caused by the change in the setting parameter, namely, the respiratory rate, of the ventilator. Regarding the alarm transfer chain corresponding to the generated alarm information, the ventilator is at a front end, and the monitor is at a rear end. Therefore, an initial alarm level of the respiratory alarm generated by the rear-end device, namely, the monitor, is lowered. For example, if an initial alarm level of the respiratory alarm generated by the monitor is medium, it is then lowered to low.

For another example, a low respiratory rate set for a ventilator may result in an alarm of the monitor that a blood oxygen value is excessively low. Certainly, the ventilator itself may also issue an alarm that a blood oxygen value is excessively low. Therefore, it is considered in the disclosure that there is an association between the excessively low respiratory rate set for the ventilator and the alarm of the monitor that the blood oxygen value is excessively low in terms of alarm causes, and the alarm generated by the monitor that the blood oxygen value is excessively low is caused by the change in the setting parameter, namely, the respiratory rate, of the ventilator. Regarding the alarm transfer chain corresponding to the generated alarm information, the ventilator is at the front end and the monitor is at the rear end. Therefore, an initial alarm level of the alarm generated by the rear-end device, namely, the monitor, that the blood oxygen value is excessively low is lowered. For example, if an initial alarm level of the alarm generated by the monitor that the blood oxygen value is excessively low is medium, it is then lowered to low.

For still another example, changes in setting parameters such as a hemodialysis dose of a hemodialysis device leads to infusion of a patient with a large amount of liquid, which may result in alarms of the monitor related to body temperature and excessively low blood oxygen value. Certainly, the hemodialysis device itself may also issue alarms related to body temperature and excessively low blood oxygen value. Then, it is considered that there is an association between the increased hemodialysis dose of the hemodialysis device and alarms related to body temperature and excessively low blood oxygen value in terms of alarm causes, and the alarms related to body temperature and excessively low blood oxygen value are caused by the increased setting parameter, that is, the increased hemodialysis dose of the hemodialysis device. Regarding the alarm transfer chain corresponding to the generated alarm information related to excessively low blood oxygen value, the hemodialysis device is at the front end and the monitor is at the rear end. Therefore, an initial alarm level of the alarm related to excessively low blood oxygen value generated by the rear-end device, namely, the monitor, is lowered. For example, if an initial alarm level of the alarm related to excessively low blood oxygen value generated by the monitor is medium, it is then lowered to low. Similarly, regarding the alarm transfer chain corresponding to the generated alarm related to body temperature, the hemodialysis device is at the front end and the monitor is at the rear end. Therefore, an initial alarm level of the alarm related to body temperature generated by the rear-end device, namely, the monitor, is lowered. For example, if an initial alarm level of the alarm related to body temperature generated by the monitor is medium, it is then lowered to low.

In some embodiments, an initial alarm level of each piece of alarm information is related to the corresponding parameter alarm level, and the parameter alarm level is determined by a parameter value that triggers an alarm. For example, the lower the respiratory rate is, the higher the parameter alarm level of the respiratory alarm triggered by the respiratory rate is, and accordingly the higher the corresponding initial alarm level is.

It can be understood that each piece of specific alarm information is optimized in step 140. After alarm information generated by a device is optimized, an initial alarm level of a same type of alarm information generated by the device is unrelated to an initial level of the previously optimized alarm information. For example, after a respiratory rate is reset for the ventilator at a first moment, it causes a respiratory alarm of the monitor. If an initial alarm level of the respiratory alarm generated by the monitor is medium, after the respiratory alarm is optimized in step 140, an alarm level of the respiratory alarm is lowered to low; then, the monitor issues a respiratory alarm again at a second moment, an initial level of the respiratory alarm of the monitor at this moment is unrelated to and independent of the alarm level of the respiratory alarm generated by the monitor at the first moment that has been optimized to low, and the initial alarm level of the respiratory alarm generated by the monitor at the second moment is, for example, related to a parameter alarm level of the respiratory alarm.

In step 160, the optimized alarm information is displayed. For example, the display 30 displays the optimized alarm information.

A specific display manner may be displaying the alarm information and an optimized level of the alarm information. For example, an alarm level of the current respiratory alarm of the monitor is medium and is optimized to low, and then the respiratory alarm of the monitor and an optimized level of the respiratory alarm are displayed.

In step 180, the obtained alarm information is sorted according to an alarm level of each piece of alarm information, and each piece of sorted alarm information is displayed. For example, the display 30 displays each piece of sorted alarm information. It can be understood that sorting each piece of alarm information in step 180 means sorting optimized alarm information.

The processor 32 in the central display device performs steps and procedures of FIG. 5, FIG. 6, or FIG. 7 to implement a method for processing alarms of multiple devices. The method for processing alarms of multiple devices may be applied to a real-time alarm scenario. For example, when the multiple pieces of alarm information generated by the multiple devices are obtained in real time in step 100, the alarm information obtained in real time is optimized and displayed by means of step 120, step 140, and step 160. The method for processing alarms of multiple devices may also be applied to an alarm review scenario. For example, when the multiple pieces of alarm information generated by the multiple devices within the preset time period are obtained in step 100, the alarm information is optimized by means of step 120 and step 140, and the alarm information is sorted and displayed by means of step 180.

Figure 8:
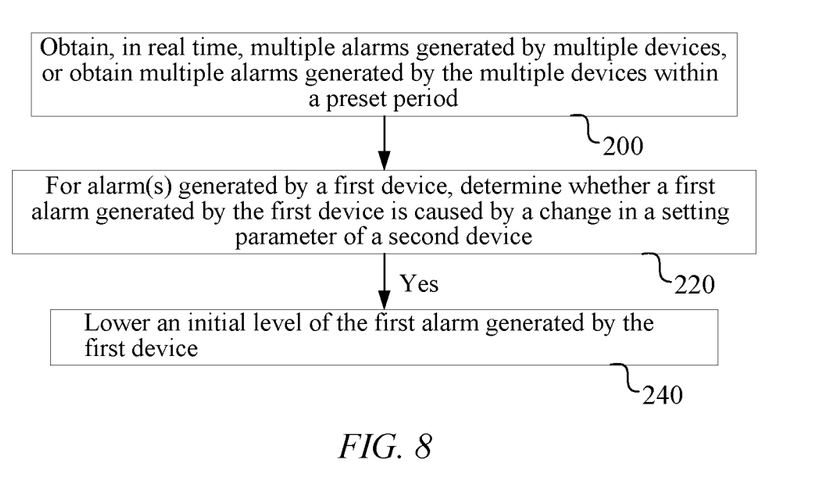
FIG. 8 is a flowchart of a method for processing alarms of multiple devices according to yet another embodiment.
Figure 9:
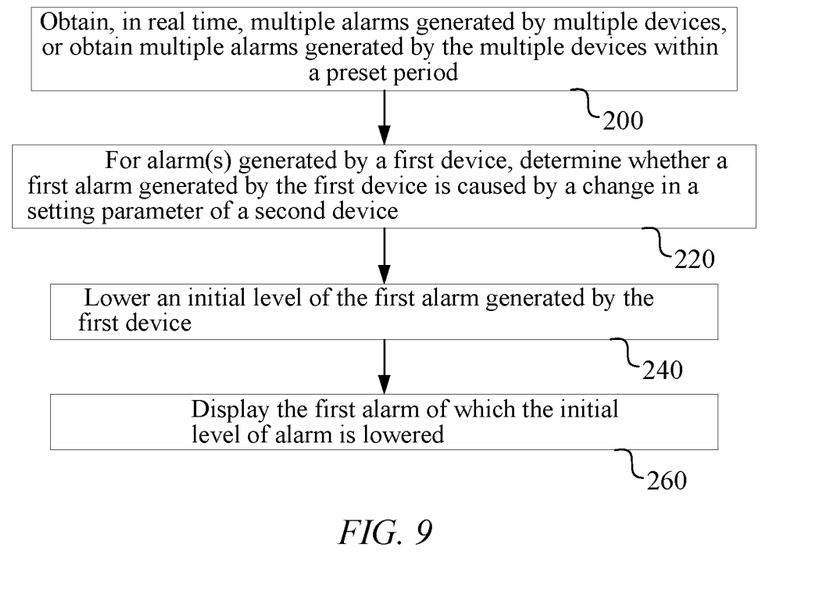
FIG. 9 is a flowchart of a method for processing alarms of multiple devices according to still yet another embodiment.
Figure 10:
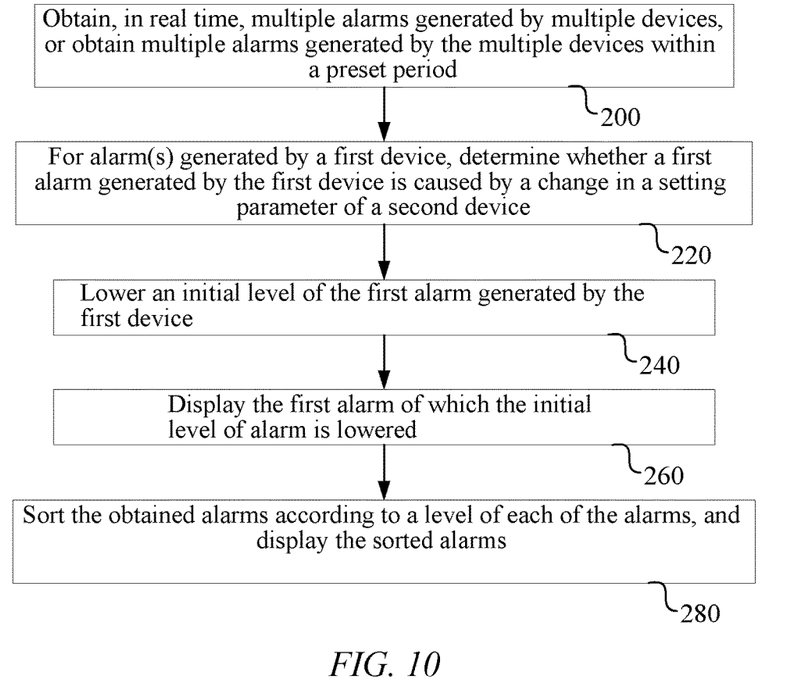
FIG. 10 is a flowchart of a method for processing alarms of multiple devices according to a further embodiment.

Referring to FIGS. 8, 9, and 10, in some embodiments, the processor 32 can invoke a number of the program instructions 36 described above to further perform the following steps.

In step 200, multiple pieces of alarm information generated by multiple devices are obtained in real time, or multiple pieces of alarm information generated by the multiple devices within a preset time period are obtained.

It can be understood that the multiple devices herein are devices that establish a connection to a central display device and can generate alarm information and transfer the alarm information to the central display device. These devices monitor and/or treat a same patient.

In step 220, for alarm information generated by any first device, whether first alarm information generated by the first device is caused by a change in a setting parameter of a second device is determined.

It can be understood that the first device and the second device herein are devices in the multiple devices mentioned in step 200 described above. In addition, herein, "first" and "second" in the first device and the second device are intended only for the convenience of describing the technical solution and for distinguishing the described objects, and do not have any order or technical meaning. When they appear in the same sentence, the first device and the second device are only two different devices. Moreover, the first alarm information generated by the first device herein is also one specific piece of alarm information in the alarm information generated by the first device. Herein, the naming method for the first alarm information is used for the convenience of description and distinguishing. Therefore, whether first alarm information generated by the first device is caused by a change in a setting parameter of a second device in step 220 refers to whether a specific piece of alarm information generated by any one of the multiple devices in step 200 is caused by a change in a setting parameter of another device in the multiple devices.

Step 220 may be implemented in multiple manners. For example, referring to FIG. 11, in some embodiments, step 220 of determining whether first alarm information generated by the first device is caused by a change in a setting parameter of a second device includes the following steps.

Figure 11:
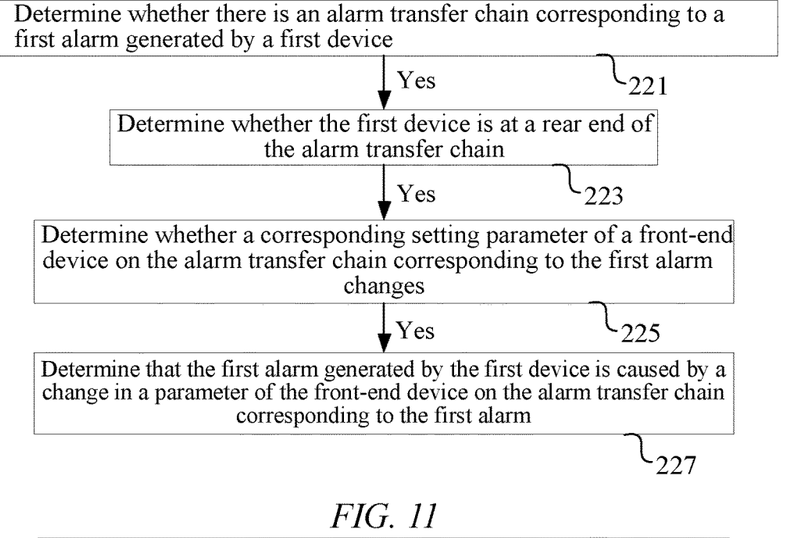
FIG. 11 is a flowchart of determining whether a first alarm generated by a first device is caused by a change in a setting parameter of a second device.

In step 221, whether there is an alarm transfer chain corresponding to the first alarm information generated by the first device is determined.

In step 223, if there is an alarm transfer chain corresponding to the first alarm information generated by the first device, whether the first device is at a rear end of the alarm transfer chain is determined.

In step 225, if the first device is at the rear end of the alarm transfer chain, whether a corresponding setting parameter of a front-end device on the alarm transfer chain corresponding to the first alarm information changes is determined.

In step 227, if the corresponding setting parameter changes, it is determined that the first alarm information generated by the first device is caused by a change in a setting parameter of the front-end device on the alarm transfer chain corresponding to the first alarm information.

The alarm transfer chain reflects the causes of alarm information, where a front-end device and a rear-end device are defined. There is a cause-and-effect relationship between the front-end device and the rear-end device, and a change in a setting parameter of the front-end device can cause an alarm of the rear-end device.

For example, a respiratory rate reset for the ventilator may cause a respiratory alarm of the monitor. Certainly, the ventilator itself may also issue a respiratory alarm. In this case, it is considered in the disclosure that there is an alarm transfer chain corresponding to the respiratory alarm generated by the monitor. On this alarm transfer chain, the monitor is at a rear end of the alarm transfer chain and is a rear-end device, and the ventilator is at a front end of the alarm transfer chain and is a front-end device. The front-end device on the alarm transfer chain corresponding to the respiratory alarm of the monitor is the ventilator, and a corresponding setting parameter, namely, the respiratory rate, of the ventilator has changed. Then, it is determined that the respiratory alarm of the monitor on the corresponding alarm transfer chain is caused by the change in the setting parameter of the front-end device, namely, the ventilator.

For another example, a low respiratory rate set for the ventilator may cause an alarm of the monitor that a blood oxygen value is excessively low. Certainly, the ventilator itself may also issue an alarm that a blood oxygen value is excessively low. Therefore, it is considered in the disclosure that there is an alarm transfer chain corresponding to the alarm generated by the monitor that the blood oxygen value is excessively low. On this alarm transfer chain, the monitor is at a rear end of the alarm transfer chain and is a rear-end device, and the ventilator is at a front end of the alarm transfer chain and is a front-end device. The front-end device on the alarm transfer chain corresponding to the alarm of the monitor that the blood oxygen value is excessively low is the ventilator, and a corresponding setting parameter, namely, the respiratory rate, of the ventilator has changed. Then, it is determined that the alarm of the monitor that the blood oxygen value is excessively low on the corresponding alarm transfer chain is caused by the change in the setting parameter of the front-end device, namely, the ventilator.

For still another example, changes in setting parameters such as a hemodialysis dose of the hemodialysis device lead to infusion of a patient with a large amount of liquid. This may cause alarms related to body temperature and an excessively low blood oxygen value. Certainly, the hemodialysis device itself may also issue alarms related to body temperature and/or an excessively low blood oxygen value. Therefore, it is considered in the disclosure that there is an alarm transfer chain corresponding to the alarm related to body temperature generated by the monitor, and there is also an alarm transfer chain corresponding to the alarm related to an excessively low blood oxygen value generated by the monitor. On the two alarm transfer chains, the monitor is at a rear end of each of the alarm transfer chains and is a rear-end device, and the hemodialysis device is at a front end of each of the alarm transfer chains and is a front-end device. The front-end device on the alarm transfer chain corresponding to the alarm related to body temperature of the monitor is the hemodialysis device, and a corresponding setting parameter, such as the hemodialysis dose, of the hemodialysis device has changed. Then, it is determined that the alarm of the monitor related to body temperature on the corresponding alarm transfer chain is caused by the change in the setting parameter of the front-end device, namely, the hemodialysis device. Similarly, the front-end device on the alarm transfer chain corresponding to the alarm of the monitor related to an excessively low blood oxygen value is the hemodialysis device, and a corresponding setting parameter, such as the hemodialysis dose, of the hemodialysis device has changed. Then, it is determined that the alarm of the monitor related to an excessively low blood oxygen value on the corresponding alarm transfer chain is caused by the change in the setting parameter of the front-end device, namely, the hemodialysis device.

Whether there is an alarm transfer chain corresponding to the first alarm information generated by the first device may be determined by the processor 32 through real-time logic, or may be determined by the processor 32 querying a predefined alarm transfer chain. For example, a number of alarm transfer chains are predefined, such as an alarm transfer chain 1 corresponding to the respiratory alarm of the monitor: the ventilator is a front-end device, the monitor is a rear-end device, and a change in the respiratory rate for the ventilator causes the respiratory alarm of the monitor; an alarm transfer chain 2 corresponding to the alarm of the monitor that the blood oxygen value is excessively low: the ventilator is a front-end device, the monitor is a rear-end device, and the excessively low respiratory rate set for the ventilator causes the alarm of the monitor that the blood oxygen value is excessively low; an alarm transfer chain 3 corresponding to the alarm of the monitor related to body temperature: the hemodialysis device is a front-end device, the monitor is a rear-end device, and the larger hemodialysis dose of the hemodialysis device causes the alarm of the monitor related to body temperature; and an alarm transfer chain 4 corresponding to the alarm of the monitor related to excessively low blood oxygen value: the hemodialysis device is a front-end device, the monitor is a rear-end device, and the larger hemodialysis dose of the hemodialysis device causes the alarm of the monitor related to an excessively low blood oxygen value; etc.

In step 240, if the first alarm information generated by the first device is caused by the change in the setting parameter of the second device, an initial alarm level of the first alarm information generated by the first device is lowered.

The following several examples are used for description.

For example, the respiratory rate reset for the ventilator may cause a respiratory alarm of the monitor, that is, the respiratory alarm generated by the monitor may be caused by the change in the setting parameter, namely, the respiratory rate, of the ventilator, the monitor is the first device, the respiratory alarm generated by the monitor is the first alarm information, the ventilator is the second device, and the alarm level of the respiratory alarm generated by the monitor may be lowered, for example, if the initial alarm level of the respiratory alarm is medium, it may then be lowered to low.

For another example, a low respiratory rate set for the ventilator may cause an alarm of the monitor that a blood oxygen value is excessively low, that is, the alarm generated by the monitor that the blood oxygen value is excessively low is caused by the change in the setting parameter, namely, the respiratory rate, of the ventilator, the monitor is the first device, the alarm generated by the monitor that the blood oxygen value is excessively low is the first alarm information, the ventilator is the second device, and the alarm level of the respiratory alarm generated by the monitor may be lowered, for example, if the initial alarm level of the respiratory alarm is medium, it may then be lowered to low.

For still another example, changes in setting parameters such as a hemodialysis dose of the hemodialysis device leads to infusion of a patient with a large amount of liquid, thereby causing alarms of the monitor related to body temperature and an excessively low blood oxygen value. In this case, two independent optimizations may be performed. In one optimization, the monitor is the first device, the alarm related to body temperature generated by the monitor is the first alarm information, the hemodialysis device is the second device, and the alarm level of the alarm related to body temperature generated by the monitor may be lowered, for example, if the initial alarm level of the respiratory alarm is medium, it may then be lowered to low. In the other optimization, the alarm of the monitor related to an excessively low blood oxygen value is the first alarm information, and the alarm level of the alarm of the monitor related to an excessively low blood oxygen value may be lowered, for example, if the initial alarm level of the alarm of the monitor related to an excessively low blood oxygen value is medium, it may then be lowered to low.

In some embodiments, an initial alarm level of each piece of alarm information is related to a parameter alarm level of the alarm information, and the parameter alarm level is determined by a parameter value that triggers an alarm. For example, the lower the respiratory rate is, the higher the parameter alarm level of a respiratory alarm triggered by the respiratory rate is, and accordingly the higher the corresponding initial alarm level is.

In step 260, the first alarm information of which the initial alarm level is lowered is displayed. For example, the display 30 displays the first alarm information of which the initial alarm level is lowered.

A specific display manner may be displaying the alarm information and a lowered level of the alarm information. For example, an alarm level of the current respiratory alarm of the monitor is medium and is lowered to low, and then the respiratory alarm of the monitor and a lowered level of the respiratory alarm are displayed.

In step 280, the obtained alarm information is sorted according to an alarm level of each piece of alarm information, and each piece of sorted alarm information is displayed. For example, the processor 32 sorts the obtained alarm information according to the alarm level of each piece of alarm information; and the display 30 displays each piece of sorted alarm information.

The processor 32 in the central display device performs steps and procedures of FIG. 8, FIG. 9, or FIG. 10 to implement a method for processing alarms of multiple devices. The method for processing alarms of multiple devices may be applied to a real-time alarm scenario. For example, when the multiple pieces of alarm information generated by the multiple devices are obtained in real time in step 200, the alarm information obtained in real time is processed and displayed by means of step 220, step 240, and step 260. The method for processing alarms of multiple devices may also be applied to an alarm review scenario. For example, when the multiple pieces of alarm information generated by the multiple devices within the preset time period are obtained in step 200, the alarm information is processed by means of step 220 and step 240, and then, the alarm information is sorted and displayed by means of step 280.

Figure 12:
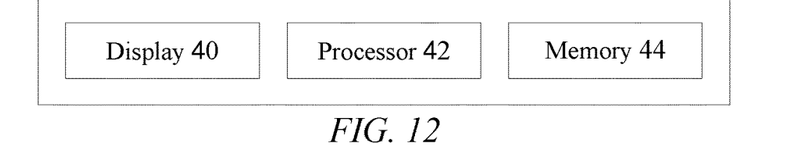
FIG. 12 is a schematic structural diagram of a device A according to an embodiment.

In some embodiments, alternatively, one (which may be named a device A) of the device 1, the device 2, the device 3, . . . , and the device N in FIG. 3 may be used to replace the central display device. The device A can be configured to monitor and/or treat a patient, and the device A establishes a connection to other devices, mentioned in the disclosure, for monitoring and/or treating a patient. The device A itself can also be configured to monitor and/or treat a patient, and it can be understood that the device A and these devices to which the device A establishes a connection are all configured to monitor and/or treat a same object, namely, a same patient. Referring to FIG. 12, a device A in some embodiments may include a display 40, a processor 42, and a memory 44. The memory 44 stores a number of program instructions 46. In other words, the device A further includes a number of program instructions 46 stored in the memory 44. The program instructions 46 can be invoked by the processor 42 to perform corresponding steps, and implement corresponding functions. Specifically, the processor 42 of the device A can invoke the number of program instructions 46 described above to perform steps and procedures illustrated in any of FIGS. 5 to 11. Certainly, it can be understood that the multiple devices involved in step 100 and step 200 in this case are the device A and the devices to which the device A establishes a connection.

The description has been made with reference to various exemplary embodiments herein. However, those skilled in the art would have appreciated that changes and modifications could have been made to the exemplary embodiments without departing from the scope herein. For example, various operation steps and assemblies for executing operation steps may be implemented in different ways according to a specific application or considering any number of cost functions associated with the operation of the system (for example, one or more steps may be deleted, modified or incorporated into other steps).

In the above embodiments, the disclosure may be implemented in whole or in part by software, hardware, firmware, or any combination thereof. In addition, as understood by those skilled in the art, the principles herein may be reflected in a computer program product on a computer-readable storage medium that is pre-installed with computer-readable program codes. Any tangible, non-transitory computer-readable storage medium can be used, including magnetic storage devices (hard disks, floppy disks, etc.), optical storage devices (CD-ROM, DVD, Blu Ray disks, etc.), flash memories, and/or the like. These computer program instructions can be loaded onto a general-purpose computer, a dedicated computer, or other programmable data processing apparatus to form a machine, such that these instructions executed on a computer or other programmable data processing apparatus can generate an apparatus that implements a specified function. These computer program instructions can also be stored in a computer-readable memory that can instruct a computer or other programmable data processing apparatus to operate in a specific manner, such that the instructions stored in the computer-readable memory can form a manufactured product, including an implementation apparatus that implements a specified function. The computer program instructions may also be loaded onto a computer or other programmable data processing apparatus, such that a series of operating steps are executed on the computer or other programmable device to produce a computer-implemented process, such that the instructions executed on the computer or other programmable device can provide steps for implementing a specified function.

Although the principles herein have been shown in various embodiments, many modifications of structures, arrangements, ratios, elements, materials, and components that are particularly suitable for specific environments and operating requirements can be made without departing from the principles and scope of the disclosure. The above modifications and other changes or amendments will be included within the scope herein.

The above specific description has been described with reference to various embodiments. However, those skilled in the art would have appreciated that various modifications and changes could have been made without departing from the scope of the disclosure. Therefore, consideration of the disclosure will be in an illustrative rather than a restrictive sense, and all such modifications will be included within the scope thereof. Likewise, the advantages of various embodiments, other advantages, and the solutions to problems have been described above. However, the benefits, advantages, solutions to problems, and any elements that can produce these, or solutions that make them more explicit, should not be interpreted as critical, necessary, or essential. The term "comprise", "include", and any other variants thereof used herein are non-exclusive, so that the process, method, document, or device that includes a list of elements includes not only these elements, but also other elements that are not explicitly listed or do not belong to the process, method, system, document, or device. Furthermore, the term "coupling" and any other variations thereof used herein refer to physical connection, electrical connection, magnetic connection, optical connection, communication connection, functional connection, and/or any other connection.

Those skilled in the art will recognize that many changes may be made to the details of the above-described embodiments without departing from the basic principles of the disclosure. Therefore, the scope of the disclosure should be determined only by the claims.

What is claimed is:

1. A method for processing multiple alarms generated by multiple devices configured to monitor or treat a patient, comprising:

obtaining, in real time, the multiple alarms generated by the multiple devices, or obtaining the multiple alarms generated by the multiple devices within a preset period;

determining an association between the multiple devices in terms of alarm causes; and when at least two different devices of the multiple devices have the association in terms of alarm causes, optimizing alarms generated by the at least two different devices, wherein optimizing alarms generated by the at least two different devices comprises:

determining, between the at least two devices having the association in terms of alarm causes, a rear-end device at a rear end of an alarm transfer chain corresponding to the alarms generated by the at least two devices; and lowering an initial level of an alarm generated by the rear-end device.

2. The method of claim 1, wherein an initial level of each of the multiple alarms is related to an alarm level of a parameter, and the alarm level of the parameter is determined by a value of the parameter.

3. The method of claim 1, further comprising: displaying the optimized alarms.

4. The method of claim 1, further comprising: sorting the multiple alarms according to levels of the multiple alarms, and then displaying the sorted alarms.

5. A method for processing multiple alarms generated by multiple devices configured to monitor or treat a patient, comprising:

obtaining, in real time, the multiple alarms generated by the multiple devices, or obtaining the multiple alarms generated by the multiple devices within a preset period;

determining whether a first alarm generated by a first device of the multiple devices is caused by a change in a setting parameter of a second device of the multiple devices; and if the first alarm generated by the first device is caused by the change in the setting parameter of the second device, lowering an initial level of the first alarm generated by the first device.

6. The method of claim 5, wherein determining whether a first alarm generated by the first device is caused by a change in a setting parameter of a second device of the multiple devices comprises:

determining whether there is an alarm transfer chain corresponding to the first alarm generated by the first device;

if there is an alarm transfer chain corresponding to the first alarm generated by the first device, determining whether the first device is at a rear end of the alarm transfer chain;

if the first device is at the rear end of the alarm transfer chain, determining whether the setting parameter of the second device is changed, wherein the second device is a front-end device on the alarm transfer chain corresponding to the first alarm; and if the setting parameter is changed, determining that the first alarm generated by the first device is caused by the change in the setting parameter of the second device.

7. The method of claim 5, wherein an initial level of each of the multiple alarms is related to an alarm level of a parameter, and the alarm level of the parameter is determined by a value of the parameter.

8. The method of claim 5, further comprising: displaying the first alarm, wherein the initial level of the first alarm is lowered.

9. The method of claim 5, further comprising: sorting the multiple alarms according to levels of the multiple alarms, and displaying the sorted alarms.

10. A central display device, the central display device establishing a connection to multiple devices configured to monitor or treat a patient, and configured to generate multiple alarms and transfer the multiple alarms to the central display device, wherein the central display device comprises a display, a processor, a memory, and multiple program instructions stored in the memory, and the processor executes the multiple program instructions to perform a method for processing the multiple alarms generated by the multiple devices, the method comprising:

obtaining, in real time, the multiple alarms generated by the multiple devices, or obtaining the multiple alarms generated by the multiple devices within a preset period;

determining an association between the multiple devices in terms of alarm causes; and when at least two different devices of the multiple devices have the association in terms of alarm causes, optimizing alarms generated by the at least two different devices, wherein optimizing alarms generated by the at least two different devices comprises:

determining, between the at least two devices having the association in terms of alarm causes, a rear-end device at a rear end of an alarm transfer chain corresponding to the alarms generated by the at least two devices; and lowering an initial level of an alarm generated by the rear-end device.

11. The central display device of claim 10, wherein an initial level of each of the multiple alarms is related to an alarm level of a parameter, and the alarm level of the parameter is determined by a value of the parameter.

12. The central display device of claim 10, wherein the display is configured to display the optimized alarms.

13. The central display device of claim 10, wherein the processor executes the multiple program instructions to further sort the multiple alarms according to levels of the multiple alarms; and the display is configured to display the sorted alarms.

14. A central display device, the central display device establishing a connection to multiple devices configured to monitor or treat a patient, and configured to generate multiple alarms and transfer the multiple alarms to the central display device, wherein the central display device comprises a display, a processor, a memory, and multiple program instructions stored in the memory, and the processor executes the multiple program instructions to perform a method for processing the multiple alarms generated by the multiple devices, the method comprising:

obtaining, in real time, the multiple alarms generated by the multiple devices, or obtaining the multiple alarms generated by the multiple devices within a preset period;

determining whether a first alarm generated by a first device of the multiple devices is caused by a change in a setting parameter of a second device of the multiple devices; and if the first alarm generated by the first device is caused by the change in the setting parameter of the second device, lowering an initial level of the first alarm generated by the first device.

15. The central display device of claim 14, wherein determining whether a first alarm generated by the first device is caused by a change in a setting parameter of a second device of the multiple devices comprises:
   determining whether there is an alarm transfer chain corresponding to the first alarm generated by the first device;
   if there is an alarm transfer chain corresponding to the first alarm generated by the first device, determining whether the first device is at a rear end of the alarm transfer chain;
   if the first device is at the rear end of the alarm transfer chain, determining whether the setting parameter of the second device is changed, wherein the second device is a front-end device on the alarm transfer chain corresponding to the first alarm; and
   if the setting parameter is changed, determining that the first alarm generated by the first device is caused by the change in the setting parameter of the second device.

16. The central display device of claim 14, wherein an initial level of each of the multiple alarms is related to an alarm level of a parameter, and the alarm level of the parameter is determined by a value of the parameter.

17. The central display device of claim 14, wherein the display is configured to display the optimized alarms.

18. The central display device of claim 14, wherein the processor executes the multiple program instructions to further sort the multiple alarms according to levels of the multiple alarms; and
   the display is configured to display the sorted alarms.

19. A method for processing multiple alarms generated by multiple devices configured to monitor or treat a patient, comprising:
   obtaining, in real time, the multiple alarms generated by the multiple devices, or obtaining the multiple alarms generated by the multiple devices within a preset period;
   determining an association between the multiple devices in terms of alarm causes; and
   when at least two different devices of the multiple devices have the association in terms of alarm causes, optimizing alarms generated by the at least two different devices,
   wherein determining an association between the multiple devices in terms of alarm causes comprises:
   determining whether a first alarm generated by a first device of the multiple devices is caused by a change in a setting parameter of a second device of the multiple devices.

20. A central display device, the central display device establishing a connection to multiple devices configured to monitor or treat a patient, and configured to generate multiple alarms and transfer the multiple alarms to the central display device, wherein the central display device comprises a display, a processor, a memory, and multiple program instructions stored in the memory, and the processor executes the multiple program instructions to perform a method for processing the multiple alarms generated by the multiple devices, the method comprising:
   obtaining, in real time, the multiple alarms generated by the multiple devices, or obtaining the multiple alarms generated by the multiple devices within a preset period;
   determining an association between the multiple devices in terms of alarm causes; and
   when at least two different devices of the multiple devices have the association in terms of alarm causes, optimizing alarms generated by the at least two different devices,
   wherein determining an association between the multiple devices in terms of alarm causes comprises:
   determining whether a first alarm generated by a first device of the multiple devices is caused by a change in a setting parameter of a second device of the multiple devices.

* * * * *